(12) United States Patent
Deutsch

(10) Patent No.: US 12,421,018 B2
(45) Date of Patent: Sep. 23, 2025

(54) MANUALLY RECHARGEABLE AND REUSABLE AEROSOL CAN AND METHOD

(71) Applicant: Mind 2 Make Inc., Brooklyn, NY (US)

(72) Inventor: Joseph Deutsch, Brooklyn, NY (US)

(73) Assignee: Mind 2 Make Inc., Brooklyn, NY (US)

( * ) Notice: Subject to any disclaimer, the term of this patent is extended or adjusted under 35 U.S.C. 154(b) by 200 days.

(21) Appl. No.: 18/244,035

(22) Filed: Sep. 8, 2023

(65) Prior Publication Data

US 2024/0083665 A1 Mar. 14, 2024

Related U.S. Application Data

(60) Provisional application No. 63/404,614, filed on Sep. 8, 2022.

(51) Int. Cl.
| | | |
|---|---|---|
| *B65D 83/42* | (2006.01) | |
| *A61M 11/00* | (2006.01) | |
| *A61M 11/02* | (2006.01) | |
| *A61M 11/04* | (2006.01) | |
| *B05B 11/00* | (2023.01) | |
| *B65D 83/14* | (2006.01) | |
| *B65D 83/384* | (2025.01) | |

(Continued)

(52) U.S. Cl.
CPC .......... *B65D 83/42* (2013.01); *A61M 11/006* (2014.02); *A61M 11/02* (2013.01); *A61M 11/04* (2013.01); *B05B 11/0097* (2013.01); *B65D 83/384* (2013.01); *B65D 83/70* (2013.01); *B65D 83/75* (2013.01); *B65B 31/04* (2013.01); *B65D 83/14* (2013.01); *B65D 83/20* (2013.01); *B65D 83/38* (2013.01); *B65D 83/425* (2013.01); *B65D 2583/005* (2013.01)

(58) Field of Classification Search
CPC ...... B65D 83/42; B65D 83/70; B65D 83/384; B65D 2583/005; B65D 83/14; B65D 83/38; B65D 83/425; B65D 83/20; A61M 11/02; A61M 11/04; B05B 11/0097; B65B 31/04
USPC .......................................................... 222/394
See application file for complete search history.

(56) References Cited

U.S. PATENT DOCUMENTS 3,053,422 A * 9/1962 Tenison ............... B65D 83/643
    222/399
3,955,720 A * 5/1976 Malone ................. B05B 9/0822
    222/401

(Continued)

FOREIGN PATENT DOCUMENTS

BR    MU9102089 U2    8/2013
KR    102168030 B1    10/2020
(Continued)

OTHER PUBLICATIONS

Wacaco Nanopresso Portable Espresso Maker, User Manual, Jan. 2018, four pages.

(Continued)

*Primary Examiner* — David P Angwin
(74) *Attorney, Agent, or Firm* — Shlomo S. Moshen; David W. Barman

(57) ABSTRACT

The present invention provides a manually rechargeable and reusable aerosol can system and method for refilling an aerosol can, the system comprising a container, a trigger mechanism, an air compressing mechanism and an interfacing mechanism. In one embodiment, the air compressing mechanism is a vane compressor.

12 Claims, 6 Drawing Sheets

(51) Int. Cl.
    *B65D 83/70*     (2006.01)
    *B65B 31/04*     (2006.01)
    *B65D 83/20*     (2006.01)
    *B65D 83/38*     (2006.01)

(56) References Cited

U.S. PATENT DOCUMENTS

| | | | | |
|---|---|---|---|---|
| 3,998,361 | A * | 12/1976 | Arena | B05B 9/0822 |
| | | | | 222/402.1 |
| 4,147,284 | A * | 4/1979 | Mizzi | B05B 9/0822 |
| | | | | 222/401 |
| 4,202,470 | A * | 5/1980 | Fujii | B65D 83/62 |
| | | | | 141/20 |
| 4,341,330 | A * | 7/1982 | Mascia | B65D 83/14 |
| | | | | 222/402.1 |
| 4,972,975 | A * | 11/1990 | Fuhrig | B05B 9/0811 |
| | | | | 222/394 |
| 5,131,569 | A * | 7/1992 | Hodgson | B65D 83/75 |
| | | | | 222/401 |
| 5,179,982 | A * | 1/1993 | Berube | B65D 83/38 |
| | | | | 222/105 |
| 5,238,150 | A * | 8/1993 | Williams | B65D 83/32 |
| | | | | 222/386 |
| 5,405,060 | A * | 4/1995 | von Schuckmann | |
| | | | | B05B 7/2427 |
| | | | | 222/401 |
| 5,460,300 | A * | 10/1995 | Tritsch | B65D 83/38 |
| | | | | 222/402.1 |
| 5,823,399 | A * | 10/1998 | Gartner | B05B 11/00446 |
| | | | | 222/401 |
| 6,375,047 | B1 * | 4/2002 | Herda | B67D 7/72 |
| | | | | 222/394 |
| 9,387,976 | B2 * | 7/2016 | Geis | B65D 83/384 |
| 9,505,509 | B2 * | 11/2016 | Smith | B65D 83/425 |
| 9,918,582 | B2 | 3/2018 | Song et al. | |
| 9,919,862 | B2 * | 3/2018 | Smith | B65D 83/62 |
| D823,033 | S * | 7/2018 | Cailleton | D7/300 |
| 10,421,086 | B1 * | 9/2019 | Kuligowski | B05B 7/24 |
| 2011/0297275 | A1 * | 12/2011 | Farrar | B05B 11/0056 |
| | | | | 141/113 |
| 2014/0183222 | A1 * | 7/2014 | Morrison | B05B 9/0811 |
| | | | | 222/386.5 |
| 2014/0209637 | A1 * | 7/2014 | Heatley | B65D 83/38 |
| | | | | 222/394 |
| 2015/0320948 | A1 * | 11/2015 | Eicher | B29C 65/568 |
| | | | | 128/200.21 |
| 2018/0244460 | A1 * | 8/2018 | Zeik | B05B 15/14 |
| 2020/0061647 | A1 * | 2/2020 | Park | B05B 11/0038 |
| 2022/0184648 | A1 * | 6/2022 | Maas | B05B 9/0822 |
| 2022/0356003 | A1 * | 11/2022 | Martin | B65D 83/386 |

FOREIGN PATENT DOCUMENTS

| | | |
|---|---|---|
| RU | 2692992 C9 | 8/2019 |
| WO | 2022049341 A1 | 3/2022 |

OTHER PUBLICATIONS

International search report (ISR) and Written Opinion (WO) mailed on Nov. 17, 2023 for PCT App. No. PCTUS2332311 filed on Sep. 8, 2023, seven pages.

* cited by examiner

MANUALLY RECHARGEABLE AND REUSABLE AEROSOL CAN AND METHOD

RELATED APPLICATIONS

The present application claims benefit of priority to Provisional U.S. Patent Application No. 63/404,614 filed Sep. 8, 2022, the aforementioned application being incorporated by reference in its entirety.

FIELD OF THE INVENTION

The present invention relates to a manually rechargeable and reusable aerosol can system and method employing a self-contained manual air compressor.

BACKGROUND OF THE INVENTION

Aerosol cans contain two different substances: the liquid product you're interested in releasing (e.g., paint, detergent, or hairspray) and a compressed (pressurized) gas as propellant that provides the force to expel the liquid product from the aerosol can and turn it into an aerosol cloud (such as when using a low viscosity fluid) or an aerated gel (such as when using a high viscosity fluid). Alternatively, the liquid product can be the result of a solid powder or tablet dissolved by a solute to make either a low viscosity fluid or high viscosity fluid, as described above.

As an aerosol can is used, the pressure in the can is reduced, partly because the available volume inside the can increases (as the liquid product is used up) and partly because some of the compressed gas is released with the liquid product. As a result, the aerosol can may no longer discharge the remaining liquid product, which is wasteful. Consumers must then purchase new (pre-filled) aerosol cans, which can become costly, especially when compared with just the cost of the liquid product and propellant. Finally, the discarded aerosol cans, both those with remaining liquid product and those that are completely empty, constitute harmful environmental waste. Additionally, in some cases, the discarded aerosol can may contain leftover propellant, which when released is harmful to the environment.

To address the aforementioned problems, reusable (i.e., rechargeable) aerosol cans have been developed. The reusable cans require repressurizing the cans with an air compressor or manual air pump, or a compressed air cartridge, to a desired pressure (e.g., 90 Psi). However, this requires purchasing such devices as well as having them on hand. Furthermore, the user must be familiar with the specification of the reusable aerosol can to determine how much pressure it can tolerate upon refill.

There has been a long unmet need for a reusable aerosol can that does not require additional devices and has a simple and safe repressurizing mechanism. The present invention addresses this need.

SUMMARY OF THE INVENTION

The present invention is a manually rechargeable and reusable aerosol can and method for refilling an aerosol can. In one embodiment, the aerosol can includes a container having an internal cavity adapted to contain dispensable materials including at least a liquid product and a propellant, a trigger mechanism for controlling the release of the dispensable materials, an air compressing mechanism (also referred to as "compressor mechanism") for pressurizing propellant in the container, and an interfacing mechanism for engaging the air compressing mechanism. A first end of the trigger mechanism is coupled to a first end of the container. A first end of the interfacing mechanism is coupled to a second end of the container.

In one embodiment, the interfacing mechanism is integral with and operatively connected to the compressor mechanism, with the compressor mechanism positioned above the interfacing mechanism. When the interfacing mechanism is coupled to the second end of the container, the compressor mechanism is disposed within the internal cavity of the container.

In one embodiment, the trigger mechanism is detachably coupled to the container.

In one embodiment, the interfacing mechanism is detachably coupled to the container.

In one embodiment, the compressor mechanism and interfacing mechanism are integrated into a single compressor module.

In one embodiment, the compressor mechanism is a vane compressor and the interfacing mechanism is a rotator device.

In one embodiment, the compressor mechanism (e.g., vane compressor) is disposed within the internal cavity of the container, proximate to the bottom of the internal cavity.

In one embodiment, the reusable aerosol can further includes a drive mechanism (or "drivetrain") configured to transmit power (i.e., rotational motion) from the interfacing mechanism to the compressor mechanism.

In one embodiment, the aerosol can further includes a mechanical leverage mechanism coupled to assist in reducing the force required to turn the rotary dial.

In one embodiment, the aerosol can further includes a pressure regulating valve, which may be disposed within a sidewall of the container or within the trigger mechanism.

As is generally understood in the art, a propellant is any substance in the container that, when pressure higher than atmospheric pressure is applied, will carry the container's inner content through the outlet and exit the container.

DETAILED DESCRIPTION OF THE EMBODIMENTS

Figure 1:
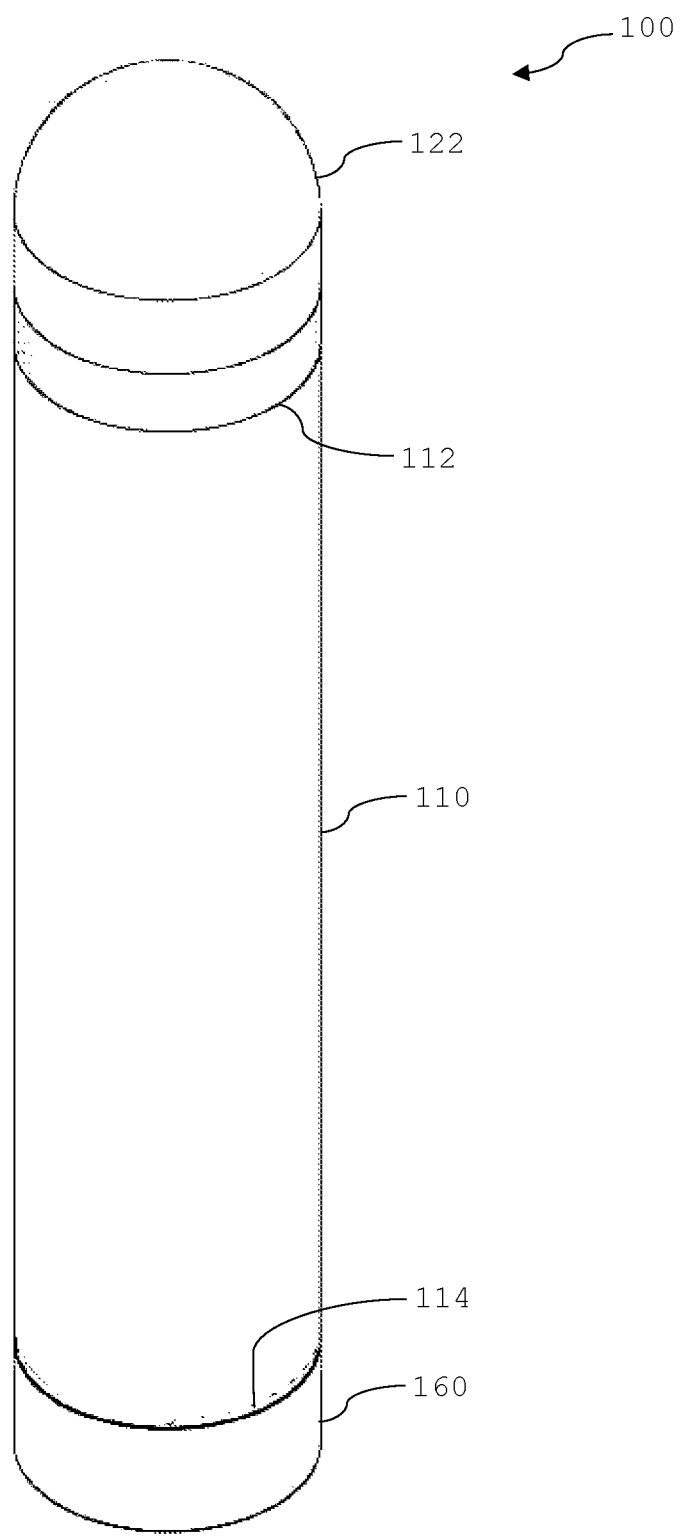
FIG. 1 is a side elevational view of a capped reusable aerosol can according to one embodiment of the present invention.

Reference will be made in detail to the embodiments of the disclosure, examples of which are illustrated in the accompanying drawings. Additional embodiments, not illustrated in the accompanying drawings, are also disclosed. Similar reference characters denote similar elements throughout the several views. The presentation of reference numerals within parentheses indicates that the mentioned reference numeral appears in a figure other than the figure(s) under discussion or is disclosed in an embodiment not presented in the drawings.

Figure 2:
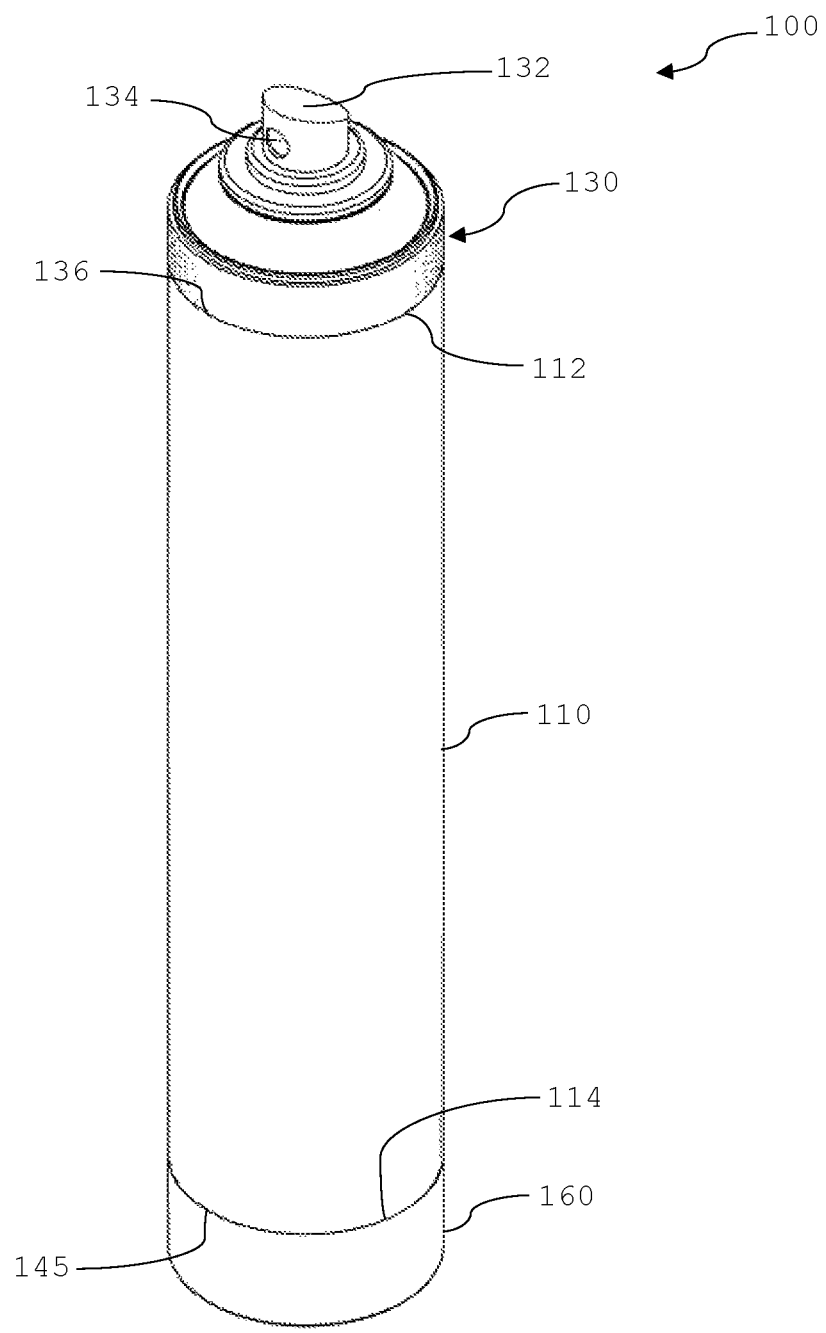
FIG. 2 is a side elevational view of the uncapped reusable aerosol can of FIG. 1.
Figure 3:
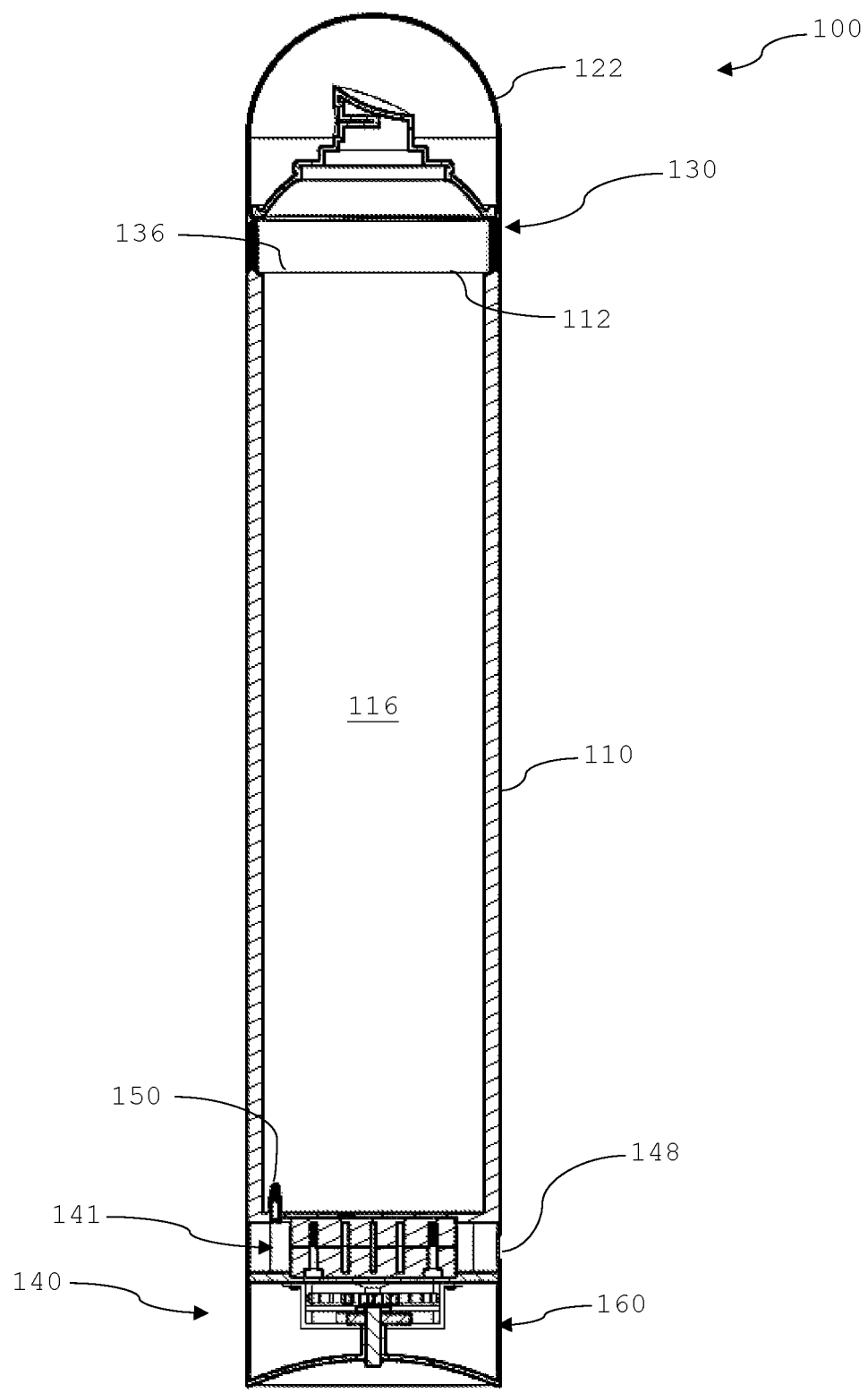
FIG. 3 is a side elevational view in section of a reusable aerosol can according to one embodiment of the present invention.

In one embodiment, as shown in FIGS. 1 to 3, a reusable aerosol can 100 includes a container 110 having an internal cavity adapted to contain dispensable materials including at least a liquid product and a propellant (see FIG. 3), a trigger mechanism 130 for controlling the release of the dispensable materials (see FIGS. 2 and 3), an air compressing (actuator) mechanism 141 for pressurizing propellant in container 110 (see FIG. 3), and an interfacing mechanism 160 for engaging air compressing mechanism 141. In one embodiment, air compressing mechanism 141 and interfacing mechanism are integrated, forming a single compressor module 140. In one embodiment air compressing mechanism 141 is coupled to the interfacing mechanism 160 via a mechanical leverage system, including but not limited to, a gear train and a strain wave gear system. In one embodiment, container 110, trigger mechanism 130 and compressor module 140 are detachably connected into one piece, and the three parts are in vertical threaded connection to form a cylinder after assembly. (Other embodiments include alternate coupling means, including, but not limited to, a twist lock connection, a quick release, a spring-loaded collar, and a crimp connection where the bottom/base of reusable can 100 would have to open.) A first or lower edge 136 of trigger mechanism 130 extends from a first or upper edge 112 of container 110 (see FIGS. 2 and 3), and a first or upper edge 145 of compressor module 140 extends from a second or lower edge 114 of container 110. (It should be understood that the aerosol can (100) may be configured with an overlap as between the first edge (112) of container (110) and first edge (136) of trigger mechanism (130), and the same as between second edge (114) of container (110) and first edge (145) of compressor module (140). Accordingly, the aforementioned structures may be referred to as extending from respective first or second "ends," which connotes broader, proximate areas, rather than edges. It should also be understood from the drawings that first or upper edge 145 of compressor module 140 is also a first or upper edge of interfacing mechanism 160, and may be referred to interchangeably.) Air compressing mechanism 141 forms a compressor chamber when second (lower) edge 114 of container 110 is coupled to first (upper) edge 145 of compressor module 140 (see FIG. 3). (The compressor chamber is described below in further detail.) A removable cap 122 is provided for covering trigger mechanism 130 when aerosol can 100 is not in use (see FIGS. 1 and 3). While cap 122 is shown as dome-shaped, a cap may be provided having a shallower or flatter top shape, or a different height, depending on need. Cap 122 may also be configured with a locking mechanism to prevent unintended removal of the cap.

As described above, a reusable aerosol can is provided in which both trigger mechanism 130 and compressor module 140 are detachably coupled to container 110. This configuration allows a user to refill container 110 from its first end 112 when it is only detached from trigger mechanism 130, or from its second end 114 when it is only detached from compressor module 140 (and providing that container 110 is inverted at the time of refilling from second end 114). Additionally, it is easier to clean container 110 when trigger mechanism 130 and compressor module 140 are detached from container 110. Other embodiments include where only one of trigger mechanism (130) and compressor module 140 is detachable from their respective first and second edges (112, 114) of container (110). (The terms "detachable" and "detachably coupled" are used herein interchangeably.)

Figure 5:
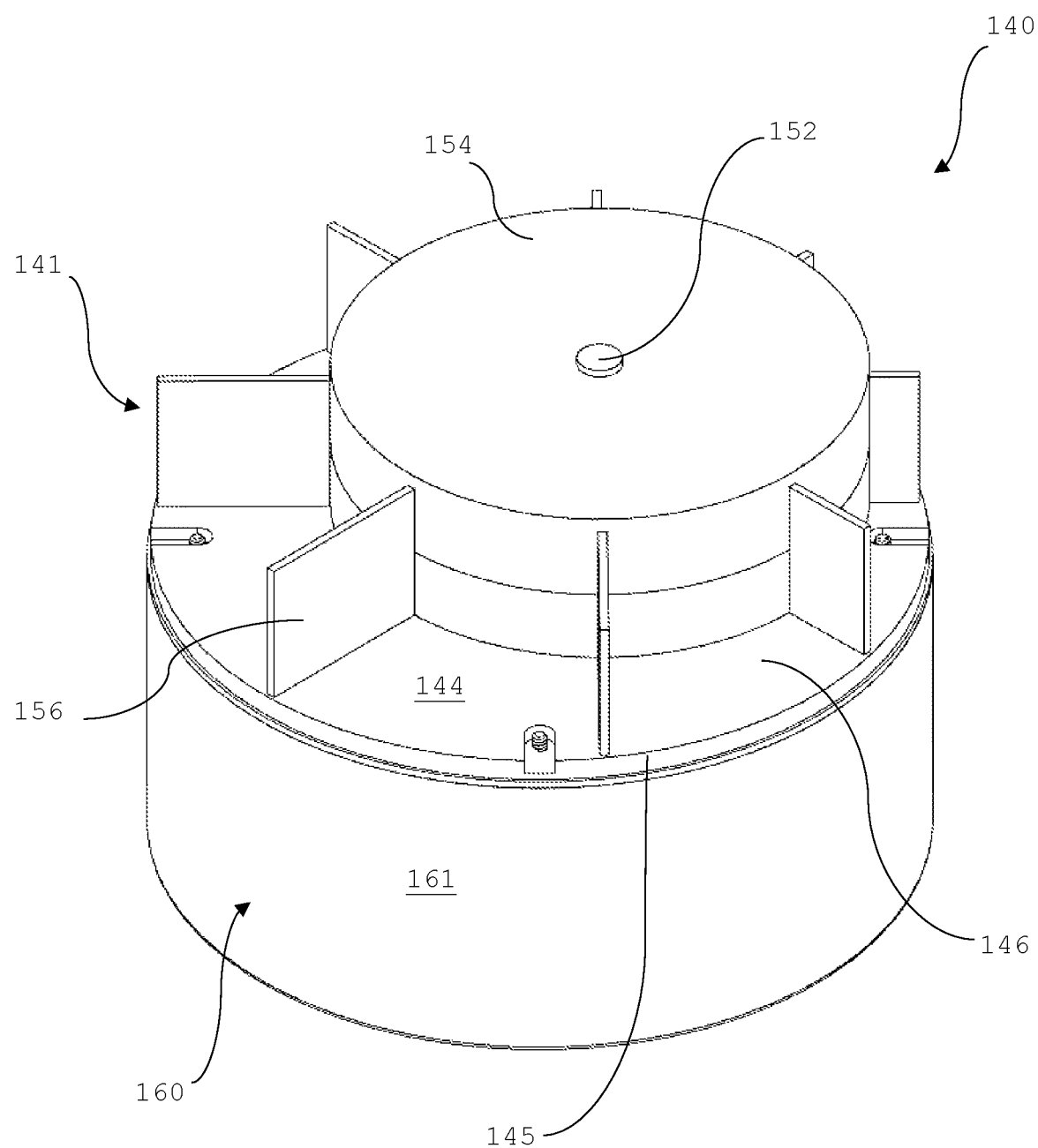
FIG. 5 is a perspective view of the compressor module of the reusable aerosol can of FIG. 3.

In one embodiment, as described above, interfacing mechanism 160 is integral with, and operatively connected to, compressor mechanism 141. As shown in FIG. 5, compressor mechanism 141 is positioned above interfacing mechanism 160; in particular, base surface 144 of compressor chamber is coupled to first or upper edge 145 of outer wall 161 of interfacing mechanism 160.

In one embodiment, additionally shown in FIG. 2, an uncapped trigger mechanism 130 includes a trigger 132 and an outlet orifice 134.

In one embodiment, interfacing mechanism (160) is configured with features to couple with an external accessory that assists in engaging the air compressor mechanism, including but not limited to, a motor.

Figure 4:
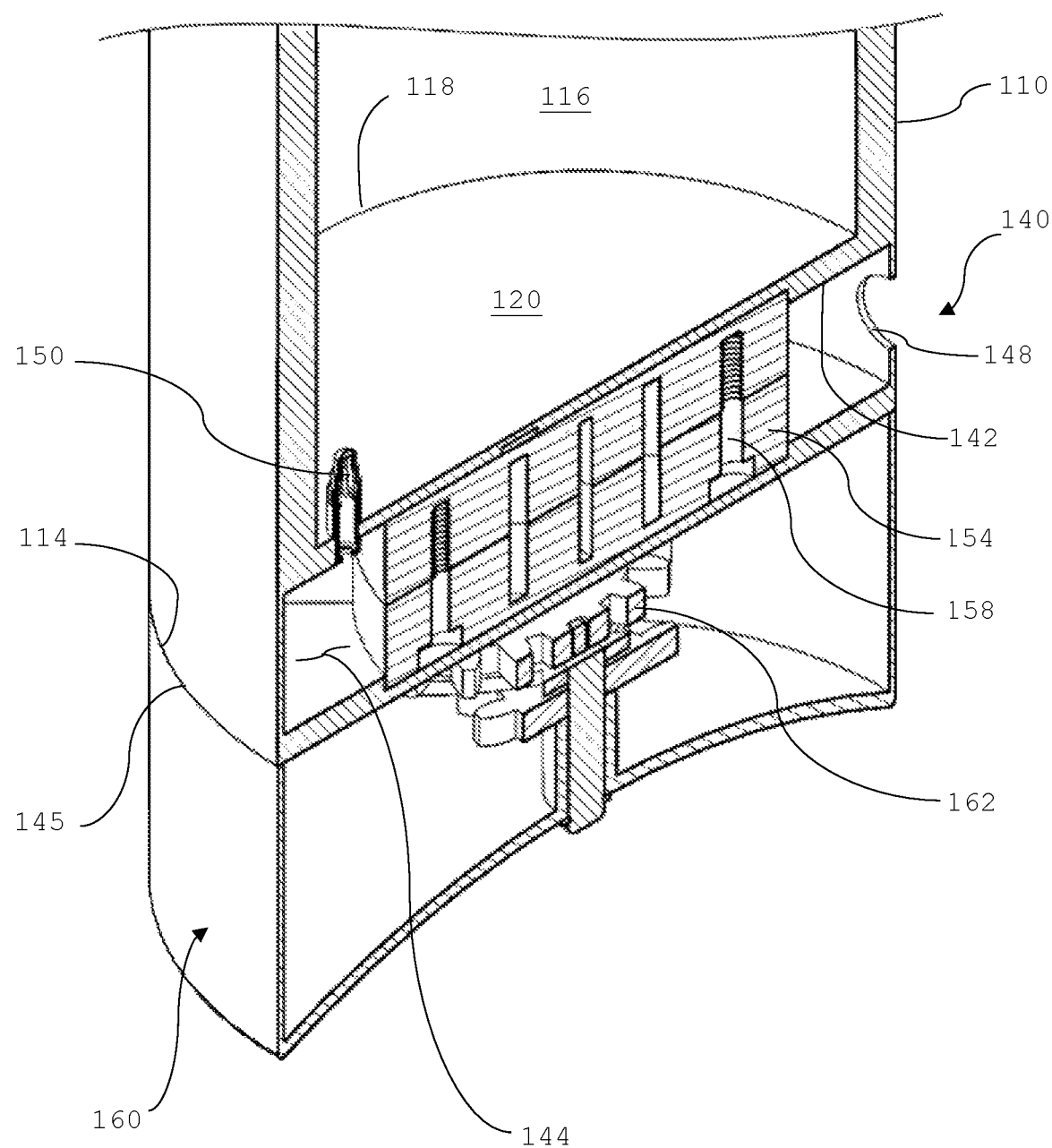
FIG. 4 is a partial perspective view, cross section of the bottom portion (i.e., compressor module) of the reusable aerosol can of FIG. 3.

In reference to FIG. 4, it is understood that the figure shows a partial (i.e., cut-away) perspective, cross section view of the bottom portion of the reusable aerosol can of FIG. 3.

Figure 6:
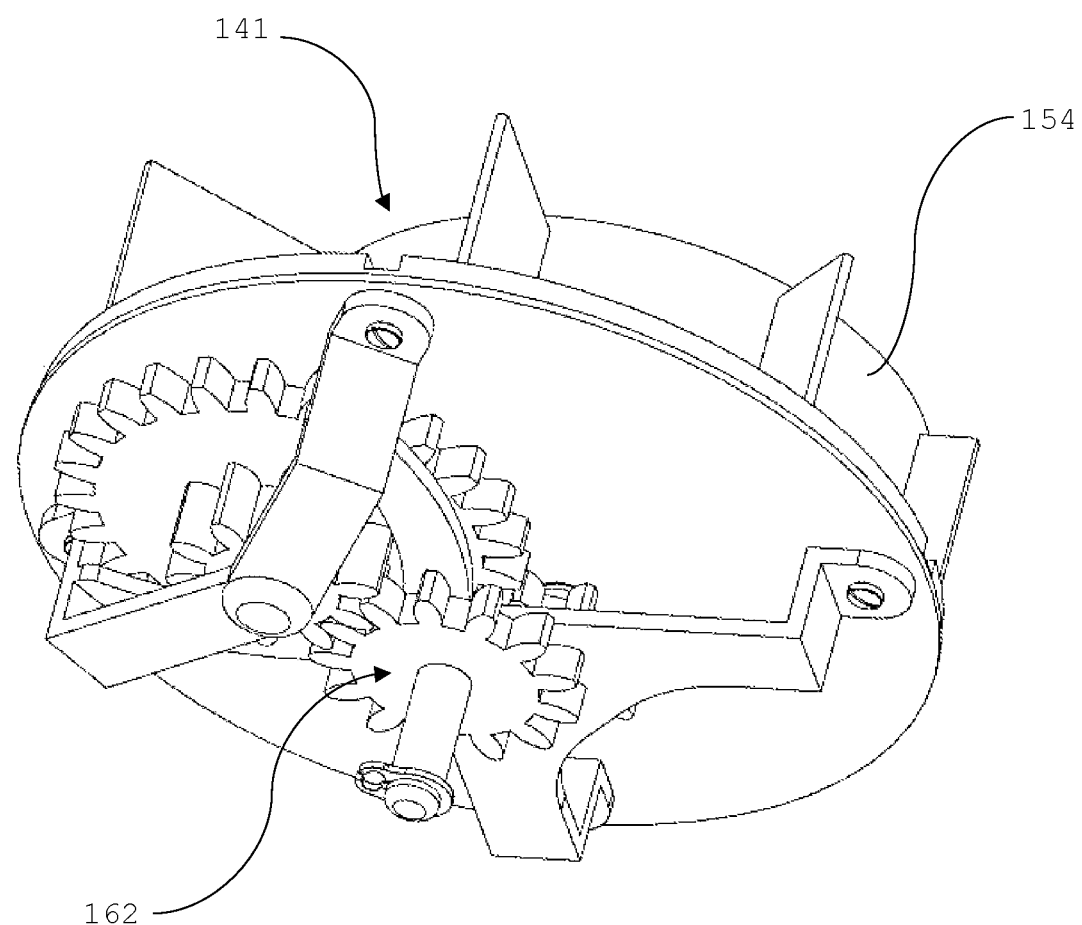
FIG. 6 is a perspective view of the drivetrain of the reusable aerosol can of FIG. 3.

In one embodiment, as shown in FIGS. 4 to 6, compressor mechanism 141 is a vane compressor. As is generally known in the art, a vane compressor (or rotary compressor) is a type of positive displacement compressor that is used to compress gases and deliver it at a higher pressure. In the embodiment(s) shown in FIGS. 3 to 6, vane compressor 141 comprises a cylindrical housing or compressor wall (which is part of the sidewall 116 of container 110, and which is shown in FIG. 3), a rotor 154 having a plurality of adjustable rotary vanes 156, an inlet 148 and an outlet 150 (see FIGS. 3 and 4). During operation, vanes 156 extend radially from an off-center drive shaft 152. As shaft 152 rotates, vanes 156 slide in and out of respective slots 158 in rotor 154 (see FIG. 4) to maintain contact with compressor wall 116, which creates respective mini-chambers 146 of varying sizes. Ambient air enters through inlet 148, into what is typically the initially largest mini-chamber. As vanes 156 rotate they retract, causing mini-chamber 146 to get smaller and compress the air contained therein. The resultant compressed air exits through outlet 150 into the internal cavity of container 110, at which point the respective mini-chamber 146 that just released its compressed air is at its smallest dimension.

The above-referenced "compressor chamber" refers to the space on the inner side of sidewall 116 and between upper end 142 and lower end (or base) 144 (see FIG. 4). It should be understood that "sidewall 116" is the cylindrical wall forming container 110, which has an outer side and an inner side.

In one embodiment, as shown in FIGS. 3 and 4, air inlet 148 is disposed in the sidewall 116 between upper end 142 and lower end (or base) 144 of the above-described compressor chamber. Outlet valve 150 is disposed in a horizontal dividing wall having base 120 of the internal cavity as its top surface and upper end 142 of the compressor chamber as its bottom surface.

In one embodiment, as shown in FIGS. 3, 4 and 6, interfacing mechanism 160 is a rotator (or mechanical dial), which when operated by a user, drives vane compressor 141. (However, other known devices may be adopted to drive vane compressor 141.) The rotator is configured to rotate about an axis. The vane compressor is coupled to the rotator and is configured to compress air (or other desired gases or substances) when the rotator is engaged (i.e., rotated).

In one embodiment, as shown in FIGS. 3, 4 and 6, aerosol can 100 further includes a drivetrain 162, which is configured to transmit power from rotator 160 to vane compressor 141. As shown in FIG. 6, drivetrain 162 includes four gears;

however, a different number of gears may be provided as needed. In one embodiment, a mechanical leverage device is also utilized to give the user a mechanical advantage when engaging the pressurizing system. As would be known in the art, drivetrain 162 may also be configured as a gear reduction to provide mechanical advantage. The drivetrain and mechanical advantage system may be the same device or system or have the same or similar configuration. In particular, the drivetrain that is used to transmit power from the interfacing mechanism to the compressor mechanism may be configured to be a system of mechanical advantage, which could reduce the force required to engage the interfacing mechanism and drive the compressor.

In one embodiment, as shown in FIGS. 3 and 4, inlet 148 is configured without a sealing mechanism. In another embodiment, a sealing mechanism is provided, whereby inlet (148) is sealed once the compressor chamber has been filled with ambient air.

In one embodiment, as shown in FIGS. 3 and 4, outlet 150 is configured with a one-way pressure valve to ensure that the pressurized air does not leak back into the compressor chamber.

Pressurizing System and Method

In applications where the reusable aerosol can will be used for a dedicated substance (e.g., a particular formulation of deodorant), the device is configured to reach only the required pressure. The air pressure is a result of the eccentric rotation of the rotor (154) and is determined by the volume reduction of the air that enters inlet port (148) and exits valve (150).

Pressure Regulation

To ensure the canister is not overly pressurized, in one embodiment, a valve may be integrated into reusable can (100). In one embodiment, the valve is integrated into sidewall (116) of container (110) in such position as to reduce the pressure in the interior cavity of container (110) when the valve is opened. In another embodiment, the valve is integrated into trigger mechanism (130). In an embodiment where the canister is configured for a single, or set pressure, and standardized solution, a relief valve is integrated into the device to ensure the pressure is passively regulated to a predetermined level. In one embodiment, a gauge is integrated into the device so that the user knows the level of pressurization in the canister. This includes, but is not limited to, a traditional pressure gauge or a viewing window gauge that would relate the pressure according to the level of the contents in the canister.

Trigger Mechanism

In one embodiment, trigger mechanism 130 as described above further include a valve stem, a vertical tube, a dip tube and an inlet orifice for receiving dispensable materials from container (110). The valve stem connects the outlet orifice (134) to the vertical tube, and the dip tube connects the vertical tube to the inlet orifice. There are many standard nozzles currently used on aerosol cans that basically function as a valve with a manual trigger to release the pressurized contents of the can. A nozzle with a trigger positioned on the top, or side of the device is selected as desired. For substances of higher viscosity, a larger dimeter nozzle will be used.

In one embodiment, aerosol can (100) further includes an accessory device capable of assisting interfacing mechanism (160) with engaging vane compressor (141). The accessory device may be an electric or mechanical motor or such other suitable device known in the art. The accessory device couples to at least the underside of interfacing mechanism (160).

Piston Compressor

The above-described embodiments represent some of the possible configurations of a rechargeable and reusable aerosol can. Alternate embodiments have been described in the above-referenced Provisional U.S. Patent Application No. 63/404,614, whose disclosure is incorporated by reference in its entirety. One such embodiment disclosed in the referenced provisional application includes a piston compressor. In this embodiment, the compressor module includes an interfacing mechanism, a piston compressor fitted with an O-ring and a vertical central threaded lead screw configured and extending longitudinally into the container when the compressor module is coupled to the container. In this embodiment, the container, trigger mechanism and interfacing mechanism are similar or the same as container (110), trigger mechanism (130 and interfacing mechanism (160) described above in connection with the accompanying drawings. Similarly, the trigger mechanism is coupled to a first or upper edge of the container and the compressor module is coupled to a second or lower edge of the container. The interfacing mechanism engages the piston compressor vertically axially upon the lead screw. The length of the lead screw may be varied depending on the particular application, such as how much pressure is needed. (For instance, the lead screw may extend longitudinally from 20% to 95% the length of the interior cavity of the container when the compressor module is coupled to the container. It would be understood to select a narrower range based on a particular application.) By engaging the piston compressor, the available space within the inner cavity of the container in which the liquid product and propellant are stored is made smaller, thereby increasing the pressure within the remaining available space. A strain wave gear system may be provided, which is a type of mechanical leverage mechanism, to assist the user spinning the interfacing mechanism (which may be a rotator or mechanical dial) by providing mechanical leverage. Such strain wave gear system typically comprises a fixed spline, flex spline and wave generator. The strain wave gear system is a gear reduction used to convert the higher rotation of the devices rotary dial to a higher imparted force on the piston compressor. A person having ordinary skill in the art would understand that other types of mechanical leverage mechanisms may be equally suitable.

In one embodiment, the piston compressor is configured to snap into place once the desired compression has been reached. In another embodiment, the piston compressor is engaged by a rotating dial in the bottom of the device or a bi-stable lever action mechanism configured to lift the piston compressor and compress the air to a predetermined pressure.

The above-described piston compressor embodiment(s) may be further modified with additional compatible features disclosed above in connection with the embodiments associated with the accompanying drawings. A person having ordinary skill in the art would recognize which of the such "additional features" are compatible with the piston compressor embodiment(s). Such additional features may include, but is not limited to, a reciprocating mechanism that will continuously move the piston compressor up and down the lead screw when the rotary dial is engaged, and a pressure regulating valve (as described above).

In one embodiment, the inner cavity of the container is divided into an upper pressure chamber adapted to contain dispensable materials including at least a liquid product and a pressurized propellant, and a lower chamber adapted to contain ambient air at atmospheric pressure when the piston compressor is not engaged, and pressurized air (i.e., propellant) when the piston compressor is engaged. The term "engaged" means where the piston has left its initial position and the air is being compressed, or has been substantially fully compressed. The upper and lower chambers are separated by a horizontal dividing wall. The container has an outlet valve disposed in dividing wall to provide air communication between the upper and lower chambers. In the embodiment the lower chamber has an inlet valve and may include a sealing mechanism so as to seal the inlet valve once the lower chamber has been filled with ambient air. In this embodiment, the lead screw is extends longitudinally into lower chamber, such that when the piston compressor is engaged (i.e., actuated upwards), ambient air in the lower chamber is pressurized and forced through the outlet valve into the upper pressure chamber. As a result, the pressure inside the lower chamber drops to lower than the pressure outside the canister.

After the piston compressor is returned to its initial position (i.e., after having been actuated downwards), the sealing mechanism may be opened, causing ambient air to enter lower the chamber via the inlet valve. The relative dimensions of the upper pressure chamber and the lower chamber may be modified as needed for a particular application, such that, in one such embodiment, the upper pressure chamber has a larger size/volume as compared with the lower chamber, and in another embodiment, the lower chamber has a larger size/volume as compared with the upper pressure chamber.

The following is a list of reference numerals and associated parts as used in this specification and drawings:

| Part | Reference Numeral |
|---|---|
| Reusable can | 100 |
| Storage container ("container") | 110 |
| First (or upper) edge of container | 112 |
| Second (or lower) edge of container | 114 |
| Sidewall of container | 116 |
| Perimeter of side wall | 118 |
| Base of internal cavity | 120 |
| Cap | 122 |
| Trigger mechanism | 130 |
| Trigger | 132 |
| Outlet orifice | 134 |
| First (lower) edge of trigger mechanism | 136 |
| Compressor module | 140 |
| Air compressing mechanism (or compressor mechanism/vane compressor) forming a compressor chamber | 141 |
| First (upper) end of compressor chamber | 142 |
| Second (lower) end of compressor chamber (aka "Base" or "Base surface") | 144 |
| First (upper) edge of compressor module (aka First or upper edge of interfacing mechanism) | 145 |
| Mini-chambers | 146 |
| Inlet port | 148 |
| Outlet valve | 150 |
| Drive shaft | 152 |
| Rotor | 154 |
| Vanes | 156 |
| Slots (in Rotor) | 158 |
| Interfacing mechanism | 160 |
| Outer wall of interfacing mechanism | 161 |
| Drivetrain | 162 |

While the invention has been described in its preferred forms or embodiments with some degree of particularity, it is understood that this description has been given only by way of example and that numerous changes in the details of construction, fabrication, and use, including the combination and arrangement of parts, may be made without departing from the spirit and scope of the invention.

What is claimed:

1. A manually rechargeable and reusable aerosol can, comprising:
   a container having an internal cavity, at least a portion of said internal cavity adapted to contain dispensable materials including at least a liquid product and a propellent;
   a trigger mechanism for controlling the release of said dispensable materials;
   a compressor mechanism for pressurizing propellant in said container; and
   an interfacing mechanism integral with and operatively connected to said compressor mechanism, said compressor mechanism positioned above said interfacing mechanism;
   wherein a first end of said trigger mechanism is coupled to a first end of said container; and
   wherein a first end of said interfacing mechanism is coupled to a second end of said container, whereby when said interfacing mechanism is coupled to said second end of said container, said compressor mechanism is disposed within said internal cavity of said container.

2. The aerosol can of claim 1, wherein said trigger mechanism is detachably coupled to said container.

3. The aerosol can of claim 1, wherein said interfacing mechanism is detachably coupled to said container.

4. The aerosol can of claim 1, further comprising a drive mechanism configured to transfer rotational motion from said interfacing mechanism to said compressor mechanism.

5. The aerosol can of claim 1, wherein said compressor mechanism is a vane compressor and said interfacing mechanism is a rotator.

6. The aerosol can of claim 5, further comprising a drive mechanism configured to transfer rotational motion from said rotator to said vane compressor.

7. The aerosol can of claim 1, further comprising a pressure regulating valve.

8. The aerosol can of claim 7, wherein said pressure regulating valve is disposed within a sidewall of said container.

9. The aerosol can of claim 7, wherein said pressure regulating valve is disposed within said trigger mechanism.

10. The aerosol can of claim 1, wherein said compressor mechanism is disposed proximate to a bottom of said internal cavity.

11. The aerosol can of claim 5, wherein said vane compressor is disposed proximate to a bottom of said internal cavity.

12. The aerosol can of claim 4 further comprising a mechanical leverage mechanism to assist in reducing the force required to turn the rotary dial.

* * * * *